(12) United States Patent
Pananakis et al.

(10) Patent No.: US 8,335,554 B2
(45) Date of Patent: Dec. 18, 2012

(54) METHOD AND DEVICE FOR OBTAINING INFORMATION ABOUT A MAMMALIAN BODY

(75) Inventors: Dimitrios Pananakis, Eindhoven (NL); Paul Royston Harvey, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 621 days.

(21) Appl. No.: 12/438,246

(22) PCT Filed: Aug. 17, 2007

(86) PCT No.: PCT/IB2007/053290
§ 371 (c)(1),
(2), (4) Date: Feb. 20, 2009

(87) PCT Pub. No.: WO2008/023314
PCT Pub. Date: Feb. 28, 2008

(65) Prior Publication Data
US 2009/0192383 A1    Jul. 30, 2009

(30) Foreign Application Priority Data
Aug. 22, 2006    (EP) ..................... 06119271

(51) Int. Cl.
*A61B 5/05* (2006.01)

(52) U.S. Cl. ......... 600/411; 600/407; 600/410; 600/429

(58) Field of Classification Search ................... 600/407, 600/410, 411, 439
See application file for complete search history.

(56) References Cited

U.S. PATENT DOCUMENTS

| | | | |
|---|---|---|---|
| 5,411,730 A | 5/1995 | Kirpotin et al. | |
| 5,492,122 A * | 2/1996 | Button et al. | 600/411 |
| 5,720,976 A | 2/1998 | Kim et al. | |
| 5,752,515 A | 5/1998 | Jolesz et al. | |
| 5,810,888 A * | 9/1998 | Fenn | 607/154 |
| 6,377,834 B1 * | 4/2002 | Zhou et al. | 600/412 |
| 7,246,939 B1 | 7/2007 | Gultekin | |
| 2003/0204141 A1 | 10/2003 | Nock et al. | |
| 2004/0119070 A1 | 6/2004 | Roach et al. | |
| 2004/0176680 A1 | 9/2004 | Moonen et al. | |
| 2005/0059623 A1 | 3/2005 | Moonen | |
| 2005/0090732 A1 * | 4/2005 | Ivkov et al. | 600/411 |
| 2006/0064002 A1 | 3/2006 | Grist et al. | |
| 2006/0173283 A1 | 8/2006 | Axelsson et al. | |
| 2006/0269612 A1 * | 11/2006 | Xiang et al. | 424/489 |
| 2008/0287773 A1 | 11/2008 | Harvey | |

FOREIGN PATENT DOCUMENTS

| | | |
|---|---|---|
| JP | 8080290 A | 3/1996 |
| JP | 2002315732 A | 10/2002 |
| JP | 2005160749 A | 6/2005 |

* cited by examiner

Primary Examiner — Brian Casler
Assistant Examiner — Joel Lamprecht (57) ABSTRACT

This invention relates to a device for retrieving information about one or more states of a mammalian body comprising: (a) a magnetic resonance imaging device comprising a first set of one or more radio-frequency coils for measuring the body temperature Ti at a selected location of a mammalian body, (b) a local heating means including a second set of one or more radio-frequency coils, said second set comprising at least two channels for delivering focused radio frequency energy to said selected location of said mammalian body and raising the temperature Ti thereof, and (c) means for modulating said radio-frequency energy delivered by said second set of coils as a function of said temperature Ti in order to reach and maintain a predefined temperature Tp above the normal mammalian body temperature Tb.

20 Claims, 3 Drawing Sheets

METHOD AND DEVICE FOR OBTAINING INFORMATION ABOUT A MAMMALIAN BODY

FIELD OF THE INVENTION

The present invention relates to a method for obtaining information about a mammalian body, especially a human body. The present invention also relates to a device for performing a method for obtaining information about a mammalian body, especially a human body. The present invention also relates to various medical uses, in particular to a diagnostic method, a therapeutic treatment or a prophylactic treatment, especially a treatment based on a thermally activated drug. The present invention also relates to a system for thermodynamic, e.g. hyperthermic, therapy. The treatment may be based on information retrieved from the performance of the method or from operation of the device.

BACKGROUND OF THE INVENTION

Magnetic Resonance Imaging techniques have been proposed for achieving non-invasive and controlled hyperthermic treatment of certain diseases, for instance by achieving local radio-frequency energy deposition in order to kill cancer cells by increasing their temperature.

Another application of local radio-frequency energy deposition is the on-command release, at a selected location, of encapsulated agents, e.g. biologically active agents, like chemo-therapeutic agents within protective bio-compatible membranes. This has obvious significant benefits over an uncontrolled administration. When used in therapeutic applications such as cancer treatment, this technology results in reducing or even eliminating the toxic effects of chemo-therapeutic agents to healthy tissues. In gene therapy, the appropriate genes can be efficiently transferred, using bio-compatible membranes, to the organ containing the target cells. The formulation of an encapsulating membrane is a significant parameter in the overall design of a system for use for local drug delivery, since it dictates the triggering mechanism of release, which in turn influences the effectiveness of the method. In the recent years, a promising class of such bio-compatible membranes has been developed, including lysolipid-containing temperature sensitive liposomes which have been designed to quickly release active agents at mild temperatures in the range of about 39° to 40° C.

Known local radio-frequency energy deposition technologies used together with Magnetic Resonance Imaging techniques suffer from important limitations. When referring to prior art, U.S. Patent application N°. 2004/0199070 teaches that, in general, those technologies rely on two coils: a) an hyperthermic applicator (i.e. a radio-frequency focusing coil) operating in the frequency range of 100 MHz in order to achieve sufficient focusability for the radio-frequency field in the patient's body and b) a monitoring coil operating in the frequency range of 8-64 MHz in order to keep a sufficient separation from the c.a. 100 MHz of the radio-frequency focusing coil. To excite the magnetic resonance for imaging/monitoring purpose, the chosen magnetic resonance frequencies require magnetic field strengths in the basic field magnet of between 0.2 and 1.5 T. At such low basic field strengths, Magnetic Resonance Imaging mediated temperature determination is not very accurate.

U.S. Patent application N°. 2004/0199070 discloses a magnetic resonance apparatus and a method for operating a magnetic resonance apparatus which partly solve this problem by replacing the existing standard monitoring coil of a magnetic resonance installation by a radio-frequency transmission and reception unit having multiple antennas that can be activated independently of one another for the purpose of emitting radio-frequency radiation of prescribable phase and amplitude. This transmission and reception unit can operate (1) as a monitoring unit for the purpose of assessing the temperature with sufficient accuracy at a tumor-containing body region, and (2) as a focussing unit for the purpose of heating up this tumor-containing body region. No additional hyperthermic applicator is used. The use of the same unit at the same frequency for the purposes of monitoring and heating implies that the temperature monitoring and the heating up of the tumor-containing body region cannot be simultaneous. On the other hand, a field strength of 3T the basic field magnet was chosen such that an explicit representation of the temperatures in the examined tissue is achieved. This field strength implies that a magnetic resonance frequency of 123.2 MHz needs to be generated. This magnetic resonance frequency corresponds to a wavelength of 10-30 cm in the patient's body and 2.5 m in the air, consequently, this frequency could also be used to achieve sufficiently intense focusing of the RF energy for the heating up of the selected location. On the other hand, the transmission/reception capabilities of the focussing unit permit this unit to send Magnetic Resonance signals to the tumor-containing body region. Upon excitation, the tumor-containing region radiates RF energy in the form of magnetic resonance signals which are then intercepted by each antenna simultaneously. From a phase and amplitude differences, it was possible to derive the phases and amplitudes which were required for actuating the individual antennas in order to generate focused RF radiation in the tumor-containing body region. The antennas are then actuated using precisely these phases and amplitudes ascertained beforehand for each individual transmission antenna.

This prior art system requires the magnetic resonance installation to be such that the irradiation with the radio-frequency energy to heat the selected body location is repeatedly interrupted briefly in order to perform a magnetic resonance measurement for the purpose of ascertaining the temperature in the selected body location. Those alternated monitoring and focussing steps require numerous switching of the operation regime of the magnetic resonance installation. This has the limitations and drawbacks to impose stress on the installation, which can lead to a shortening of the life-time thereof as well as to reliability problems. Additionally, this imposes stress on the user of the installation in a non automated regime and renders automation costlier. Furthermore, U.S. Patent application N°. 2004/0199070 is silent on the issue of on-command local release of agents, e.g. biologically active agents, and the monitoring of the concentration thereof.

There is therefore a need in the art for an improved method and device for the local deposition of radio-frequency energy permitting truly simultaneously a sufficiently intense focusing of radio-frequency energy at the selected location of the body and a sufficiently accurate monitoring of the temperature at this selected location.

There is also a need in the art for an improved method and device for delivering agents, e.g. biologically active agents, enclosed within thermosensible membranes at selected locations of a mammalian body. In particular, there is a need in the art for an improved method and device wherein information about a mammalian body such as, but not limited to, the concentration of the agents, e.g. biologically active agents, at the selected location and the temperature of the selected location can be monitored simultaneously with the heating of this selected location. There is also a need in the art for solving these problems in a cost-effective manner by designing equipment that can be easily built and maintained, and that can easily be adapted to or combined with existing Magnetic Resonance Imaging equipment.

SUMMARY OF THE INVENTION

An object of the present invention is to provide an improved method for obtaining information about a mammalian body, especially a human body, and/or to provide an improved device for performing a method for obtaining information about a mammalian body, especially a human body.

The present invention also relates to various medical uses, in particular to a diagnostic method, a therapeutic treatment or a prophylactic treatment, especially a treatment based on a thermally activated drug. The present invention also relates to a system for thermodynamic, e.g. hyperthermic, therapy. The treatment may be based on information retrieved from the performance of the method or the operation of the device.

Broadly speaking, the invention is based on the unexpected finding that the delivery of focused radio-frequency energy at a selected location of a mammalian body in order to raise the temperature thereof can be performed truly simultaneously with the accurate monitoring of this temperature by operating at the same time one or more radio-frequency focusing coil and a radio-frequency monitoring coil at frequencies differing by a value comprised between 50 kHz and 25000 kHz.

The invention is also based on the unexpected finding that agents, e.g. biologically active agents, which are thermally activatable, e.g. are enclosed within a thermosensitive membrane, can be delivered by heating at a selected location of a mammalian body without making use of invasive sensors and/or without unnecessarily heating this selected location when the concentration of agents, e.g. biologically active agents, at this location is too low to be effective. The invention is also based on the unexpected finding that useful and reliable information with respect to a mammalian body can be retrieved non-invasively when Magnetic Resonance Imaging techniques are used to monitor both the concentration, at a selected location of a mammalian body, of an agent, e.g. a biologically active agent, that has been previously administered to said mammalian body, and the temperature at this selected location.

The invention is also based on the unexpected finding that the above-referred non-invasive information-retrieving methods can easily be implemented by means of a device comprising, in addition to a magnetic resonance imaging device of a known type for measuring the body temperature at a selected location of a mammalian body, a means for raising the temperature of the body locally to a desired temperature. The means for raising the temperature of the body may focus energy to a selected location of the body. For example, the means for raising the temperature may include a set of one or more radio-frequency focusing coils comprising at least two channels for delivering focused radio frequency energy to said selected location of the mammalian body and raising the temperature thereof. Means for modulating the radio-frequency energy delivered by said set of focusing coils in order to reach and maintain a predefined temperature may also be provided.

An embodiment of the present invention relates to a method of obtaining information about a mammalian body, the temperature $T_1$ of a selected location of the mammalian body having been raised by operating at a frequency $v_2$ a set of one or more radio-frequency focussing coils comprising at least two channels able to focus energy at the selected location of the mammalian body until the predefined temperature $T_p$ is obtained. This method comprises the steps of operating at a frequency $v_1$, preferably comprised between 120 and 130 MHz, a set of one or more radio-frequency monitoring coils at least partially simultaneously with the operation of the set of one or more radio-frequency focusing coils, wherein $|v_2-v_1|$ is minimum 50 kHz, preferably minimum 100 kHz, most preferably minimum 200 kHz and wherein $|v_2-v_1|$ is maximum 25000 kHz, preferably maximum 20000 kHz, most preferably maximum 10000 kHz.

This embodiment is advantageous because it permits to perform simultaneously an accurate monitoring step and a focusing step without suffering from interference.

As another additional feature, a calibration step can be performed before the rise of the temperature $T_1$ of the selected location of the mammalian body. This calibration preferably comprises the steps of (i) providing radio-frequency energy at the frequency $v_1$ from the set of one or more radio-frequency focusing coils at the selected location of the mammalian body, and (ii) receiving magnetic resonance signals at the set of one or more radio-frequency focusing coils from the selected location of the mammalian body, said signals containing location-dependent phase information and location-dependent amplitude information.

This feature is advantageous because it enables to gain information useful for the optimisation of the wave properties sent from the one or more radio-frequency focusing coils used for heating up the selected location of the mammalian body.

As another additional feature, it can be determined from the location-dependent phase information and from the location-dependent amplitude information retrieved above, for each channel of the set of one or more radio-frequency focusing coils, a phase and/or an amplitude required to produce maximal radio-frequency energy at the selected location of the mammalian body. This permits to heat up mainly the selected location of interest with limited heating up of the surrounding.

As another additional feature, the operation of the one or more radio-frequency monitoring coils performs the monitoring of the temperature $T_1$ by means of a Magnetic Resonance Imaging technique.

This feature is advantageous because monitoring the temperature of the selected location simultaneously with the rising of this temperature permits to control the heating up process accordingly and therefore to avoid harmful overheating of the selected location.

As another additional feature, the Magnetic Resonance Imaging technique referred to hereabove is an enhanced proton shift technique taking into account fat phase information, which is a more sensitive method for temperature measurement than traditional proton shift techniques.

As an additional feature, the present invention provides a useful embodiment in a situation where a thermally activatable delivery system being able to release one or more agents, e.g. biologically active agents, and an effective amount of the one or more agents, e.g. biologically active agents, have been administered to the mammalian body before the temperature of the selected location of the mammalian body has been raised, the agents, e.g. biologically active agents, being able to be released at a selected location when the temperature $T_1$ of the selected location of the mammalian body is raised to or above a predefined temperature $T_p$ above the normal mammalian body temperature $T_b$. In this embodiment, the operating of the radio-frequency monitoring coil performs the monitoring of the transient concentration of the one or more agents, e.g. biologically active agents, at the selected location of the mammalian body by means of a Magnetic Resonance Imaging technique.

This embodiment is advantageous because by monitoring the concentration of the agents, e.g. biologically active agents, it can be made sure that no heat is generated outside the time frame where the agent, e.g. the biologically active agent, is present in an effective amount at the particular location of interest.

As an additional feature within the above-described embodiment, an additional monitoring coil can be used so that one of both monitoring coils operates at a frequency $v_3$ in order to monitor said transient concentration while at least partially simultaneously, the other monitoring coil operates at a frequency $v_1$ in order to monitor said temperature $T_1$, said frequency $v_3$ being the Larmor frequency of a nucleus other than $^1H$ being selected in such a manner that $|v_3-v_2|$ is from 50 to 25000 kHz.

This feature is advantageous because it permits to simultaneously (1) heat up the selected location, (2) control that the no unnecessary heating occurs when the concentration of biologically active substances is not adequate, and (3) control that the temperature is maintained at $T_p$ and never exceeds this temperature.

As an additional feature within the above-described embodiment, one or more of the agents, e.g. biologically active agents, can be enclosed within a temperature sensitive structure able to release the one or more agents, e.g. biologically active agents, when the temperature $T_1$ of a selected location of the mammalian body is raised to a predefined temperature $T_p$ above the normal mammalian body temperature $T_b$. This feature is advantageous because the temperature-sensitive structure prevents from any contact between the agents, e.g. biologically active agents, and the mammalian body outside the selected location and selected time frame of interest.

As another additional feature, the thermally activatable delivery system is thermally activatable at a temperature $T_p$ in the range from 36° C. to 45° C., preferably in a range from 37° C. to 41° C. This has the advantage to limit the heating to temperatures that are not dangerous for the neighbouring cells of the selected location under investigation or treatment.

As another additional feature, the agents, e.g. biologically active agents, are enclosed in a temperature sensitive membrane which may comprise a liposome, for instance a lyso-lipid-containing liposome. These delivery systems have the advantage to be biocompatible and to deliver their content in narrow temperature ranges within the ranges considered as being useful for the present invention.

As another additional feature, the one or more agents, e.g. biologically active agents, used in the thermally activatable delivery system of the present invention may be selected from the group consisting of antineoplastic agents, antitumor agents, antibiotic agents, antifungal agents, anti-inflammatory agents, immunosuppressive agents, anti-infective agents, antiviral agents, anthelminthic agents, gene for gene therapy and antiparasitic agents.

As another additional feature, the transient concentration monitoring step is effected by means of Magnetic Resonance spectroscopy with the advantage to enable the measurement of this concentration in a non-invasive and simple way without the need to incorporate additional markers.

As another additional feature, the thermally activatable system may include one or more agent concentration markers such as, but not limited to, gadolinium solutions, gadolinium-impregnated microspheres, $^{13}C$, $^{15}N$, $^{31}P$, $^{23}Na$ or $^{19}F$ containing species. This feature enables to monitor their concentration by faster and more sensitive Magnetic Resonance Imaging techniques. The sensitivity can for instance be increased by increasing the amount of marker. It also facilitate the simultaneous monitoring of the local temperature at the selected location (at a frequency $v_1$) and the transient concentration at this same selected location (at a frequency $v_3$).

As another additional feature of the present invention, the set of one or more radio-frequency coils consists of two or more mono-channel radio-frequency coils. This way, the wave sources can be placed more freely at various places in the direct neighbourhood of the selected location where heating is desired.

As another additional feature, the set of one or more radio-frequency coils consists of one or more multi-channel radio-frequency coils, preferably one multi-channel frequency coil which is an economically advantageous alternative to the use of two or more mono-channel radio-frequency coils.

Another aspect of the present invention relates to a device comprising:
(i) a magnetic resonance imaging device comprising a set of one or more radio-frequency monitoring coils operating at a frequency $v_1$ for measuring the body temperature $T_1$ at a selected location of a mammalian body and/or the concentration of agents, e.g. biologically active agents, at a selected location of a mammalian body,
(ii) a set of one or more radio-frequency focusing coils, said second set comprising at least two channels, wherein said set of one or more radio-frequency focusing coils operates at a frequency $v_2$ at least 50 kHz apart and at most 25000 kHz apart from the operation frequency $v_1$ of said set of one or more radio-frequency monitoring coils, for delivering focused energy to said selected location of said mammalian body and raising the temperature $T_1$ thereof, and
(iii) means for modulating said energy delivered by said set of one or more radio-frequency focusing coils as a function of said temperature $T_1$ in order to reach and maintain a predefined temperature $T_p$ above the normal mammalian body temperature $T_b$.

This embodiment is advantageous because by providing the device with means for simultaneously (1) monitoring the temperature of the selected location and/or the concentration of the agents, e.g. biologically active agents, at the selected location (2) monitoring the rise of the temperature, the invention makes sure that no overheating occurs and/or no heat is generated outside the time frame where the agent, e.g. the biologically active agent, is present in an effective amount at the selected location of interest and the invention obtains simultaneously an accurate monitoring step and a good focusing step without suffering from interference.

As another additional feature of the device of this invention, the set of one or more radio-frequency focusing coils comprises radio-frequency emitting means for providing energy at said selected location, and radio-frequency receiving means for receiving signals containing location-dependent phase information and location-dependent amplitude information. This feature is advantageous because it permits to determine from these informations, for each channel of the second set of one or more radio-frequency coils, as yet another additional feature of this embodiment, a phase and/or an amplitude required for emitting radio-frequency energy from each channel to produce maximal radio-frequency energy from each channel at the selected location of said mammalian body. This permits to heat up mainly the selected location of interest with limited heating up of the surrounding area(s).

As another additional feature, the device of this invention may comprise an additional monitoring coil operating at a frequency $v_3$, said frequency $v_3$ being the Larmor frequency of a nucleus other than $^1H$, at least 50 kHz apart and at most 25000 kHz apart from both $v_1$. This feature is advantageous because it permits to simultaneously (1) heat up the selected location and (2) control that no unnecessary heating occurs when the concentration of biologically active substances is not adequate, and (3) control that the temperature is maintained at $T_p$ and never exceeds this temperature.

Another aspect of the present invention relates to a system for thermodynamic therapy comprising:
(i) a set of one or more radio-frequency focussing coils able to focus energy at a frequency $v_2$ at a selected location of a mammalian body to thereby locally raise the temperature $T_1$ of the mammalian body until a predefined temperature $T_p$ is obtained, and
(ii) means for obtaining information about said mammalian body by a Magnetic Resonance Imaging technique operating at a frequency $v_1$ simultaneously with the raising of the temperature $T_1$ of the selected location of the body, wherein $|v_2-v_1|$ is from 50 to 25000 kHz.

As an additional feature of this therapy system, the Magnetic Resonance Imaging technique operates by monitoring the temperature $T_1$. This feature is advantageous because monitoring the temperature of the selected location simultaneously with the rising of this temperature permits to control the heating up process accordingly and therefore to avoid harmful overheating of the selected location of the mammalian body.

As yet another additional feature, the thermodynamic therapy system of this invention may be combined with the use of a thermally activatable delivery system, the later being able to release one or more agents, e.g. biologically active agents, at a selected location of a mammalian body when the temperature $T_1$ of the selected location of the mammalian body is raised to a predefined temperature $T_p$ above the normal mammalian body temperature $T_b$, wherein the Magnetic Resonance Imaging technique operates by monitoring the transient concentration of the one or more agents, e.g. biologically active agents, at the selected location of the mammalian body.

This feature is advantageous because by monitoring the concentration of the agents, e.g. biologically active agents, it is made sure that no heat is generated outside the time frame where the agent, e.g. the biologically active agent, is present in an effective amount at the particular location of interest.

DETAILED DESCRIPTION OF THE INVENTION

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In an embodiment, the present invention relates to a method for controlling the heating of a selected location inside a mammalian body in order to achieve a predefined temperature $T_p$ sufficient to obtain a therapeutical effect (e.g. hyperthermic treatment of tumours). In order to avoid overheating of the selected location or other body locations exposed to the heating, a monitoring of the temperature $T_1$ or the temperature distribution in at least the selected location and optionally in one or more of the other body locations exposed to the heating is performed. This monitoring is operated at least partially simultaneously with the heating of the selected location inside the mammalian body. Preferably, a feed-back process is implemented in order to control the temperature $T_1$ by linking the temperature monitoring to the heating process, e.g. a controller is provided to adjust the heating process based on the output of the temperature monitoring step.

In another embodiment, the present invention relates to a method for controlling local delivery of one or more agents, e.g. biologically active agents, in order to focus the therapeutic effects of this agent to a selected location of a mammalian body. As a preliminary step to said method, one or more agents, e.g. biologically active agents, are prepared which are thermally activatable. For example, a thermally activatable agent, e.g. biologically active agent, may include a drug which is released when reaching a certain temperature $T_p$. For example, the one or more agents, e.g. biologically active agents, can be encapsulated within a temperature sensitive structure (e.g. a membrane) which is then administered to a mammalian body. A selected location inside the mammalian body where agent(s), e.g. biologically active agent(s), release is desired can then be heated to a temperature $T_p$ sufficient to cause said release due to the deterioration of the membrane physical and/or chemical properties upon heating (and consequently optimise desired effects as well as minimise potential side effects by releasing the agent, e.g. biologically active agent, only at this location). In order to permit the release of the one or more agents, e.g. biologically active agents, at the selected body location only when its concentration is adequate, the local concentration of the encapsulated one or more agents, e.g. biologically active agents, is preferably monitored. This monitoring is optionally initiated before the administration of the encapsulated one or more agents, e.g. biologically active agents, in order to determine their initial concentration at least at the selected area. This monitoring of the encapsulated one or more agents, e.g. biologically active agents, is preferably sustained until an adequate concentration is monitored and the heating process can begin. The monitoring process can also be sustained during and simultaneously to the whole controlled heating process until the local concentration of encapsulated agent, e.g. biologically active agent, is no longer adequate and the heating process can stop. This represent one way to avoid unnecessary heating of the selected location. In order to avoid overheating of the selected location or other body locations exposed to heating, it is preferred to monitor the temperature $T_1$ or the temperature distribution in at least the selected location and optionally in one or more other body locations. This monitoring step is preferably operated simultaneously with the heating of the selected location. Preferably, a feed-back process is implemented in order to control the temperature $T_1$ by linking the temperature monitoring to the heating process, e.g. a controller is provided to adjust the heating process based on the output of the temperature monitoring step.

Another embodiment of the present invention comprises a method of prevention, treatment or diagnosis of a disease in a mammalian body comprising the steps of:
(i) raising the temperature $T_1$ of a selected location of the body by a local heating means, e.g. by operating a set of one or more energy sources, preferably being able to focus energy at said selected location of the mammalian body, until a predefined temperature $T_p$ is obtained, and
(ii) monitoring the temperature $T_1$ by means of a Magnetic Resonance Imaging technique. Preferably, this monitoring is performed at least partially simultaneously with the operation of the local heating means.

Another embodiment of the present invention comprises a method of prevention, treatment or diagnosis of a disease in a mammalian body comprising the steps of:
a) administering an effective amount of one or more agents, e.g. biologically active agents, to a mammal in need thereof, the agents, e.g. biologically active agents, being thermally activatable, i.e. can be released at or above a predefined temperature $T_1$ above the normal mammal body temperature $T_b$, or at some absolute temperature. The one or more agents, e.g. biologically active agents, may be, for example, enclosed within a temperature sensitive membrane being able to release the one or more agents, e.g. biologically active agents, at or above a predefined temperature $T_1$ above the normal mammal body temperature $T_b$,
b) monitoring the transient concentration of the one or more agents, e.g. biologically active agents, at a selected location of the mammalian body where the release of the one or more agents, e.g. biologically active agents, is desired by means a Magnetic Resonance Imaging technique,
c) raising the temperature $T_1$ of said location of the body by a local heating means, e.g. by using a set of one or more energy sources, preferably being able to focus energy at said selected location of the mammalian body, until the predefined temperature $T_p$ is obtained. Preferably, this step is at least partially simultaneous with step b), and
d) monitoring said rise of the temperature $T_1$ by means of a Magnetic Resonance Imaging technique. Preferably, this monitoring step is operated at least partially simultaneously with step c).

In another embodiment, the present invention relates to a method of obtaining information about a mammalian body, e.g. about one or more states of a mammalian body, the temperature $T_1$ of a selected location of this mammalian body having been raised. By one or more states of a mammalian body, it must be understood physical, biological or chemical states of one or more locations of a mammalian body, e.g. the selected location of a mammalian body where the temperature has been raised. In particular, it relates to a temperature $T_1$ at this location and/or a concentration of an agent, e.g. a biologically active agent, at this location. This elevation of the temperature $T_1$ is operated by one or more energy source(s) preferably being able to focus energy (at a frequency $v_2$) at the selected location of interest of the mammalian body. Preferably the one or more energy source(s) are a set of one or more radio-frequency focusing coils, said set comprising at least two channels, each channel being able to emit radio-frequency energy independently of each other. The body temperature is raised until a predefined temperature $T_p$ is obtained. The method of this invention comprises the step of operating at a frequency $v_1$ a set of one or more radio-frequency monitoring coils, this set being operated for the purpose of gaining information about one or more states of the mammalian body. Preferably, the operation of this set of one or more radio-frequency monitoring coils is simultaneous with the operation of the set of one or more radio-frequency focussing coils.

In another embodiment, the present invention relates to a method of obtaining information about a mammalian body, e.g. about one or more states of a mammalian body, an effective amount of one or more agents, e.g. biologically active agents, having been previously administered to the mammalian body. The agents, e.g. biologically active agents, are preferably thermally activatable as previously defined. For example, the agents, e.g. biologically active agents, are enclosed within a temperature sensitive membrane able to release them at a selected location when the temperature $T_1$ of this selected location of the mammalian body is raised to or above a predefined temperature $T_p$ above the normal mammalian body temperature $T_b$. This elevation of temperature $T_1$ is operated by a set of one or more radio-frequency energy source(s) able to focus energy at the selected location of interest of the mammalian body. The temperature is raised until a predefined temperature $T_p$ is obtained.

Preferably, the method of this invention comprises the further steps of:
a) monitoring the transient concentration of the one or more biologically active agents at the selected location of the mammalian body by means of a Magnetic Resonance Imaging technique, and
b) monitoring the temperature $T_1$ by means of a Magnetic Resonance Imaging technique. Step (b) and preferably also step (a) are performed at least partially simultaneously with the rise of the temperature of the selected location. This means that:
step (a) is preferably performed simultaneously with the rise of the temperature at the selected location, i.e. with the operation of the set of one or more radio-frequency energy sources;
step (b) is performed simultaneously with the rise of the temperature at the selected location, i.e. with the operation of the set of one or more radio-frequency energy sources;
step (a) and step (b) are not performed simultaneously with each other because they are both accomplished by the monitoring coil at the same frequency $v_1$.

In yet another embodiment, the present invention relates to a device being able to perform each of the above methods and preferably comprising:
(i) a magnetic resonance imaging device of a known type, e.g. comprising a radio-frequency monitoring coil operating at a frequency $v_1$ for measuring the body temperature $T_1$ at a selected location of a mammalian body,
(ii) a local heating means for delivering focused energy to the selected location of the mammalian body and consequently raising the temperature $T_1$ thereof, e.g. a set of one or more radio-frequency focusing coils, said set comprising at least two channels for delivering focused radio frequency energy to the selected location of the mammalian body and consequently raising the temperature $T_1$ thereof. This set of one or more radio-frequency focusing coils operates at a frequency $v_2$ at least 50 kHz apart from the operation frequency $v_1$ of said set of one or more radio-frequency monitoring coils, preferably at least 100 kHz apart from $v_1$, most preferably at least 200 kHz apart from $v_1$.

In a particular embodiment of the present invention, step a) and step b) are performed simultaneously (i.e. together) by using one additional monitoring coil operating at a frequency $v_3$, said frequency $v_3$ being the Larmor frequency of a nucleus other than $^1$H such as $|v_2-v_3|$ is minimum 50 kHz, preferably minimum 100 kHz, most preferably minimum 200 kHz and wherein $|v_2-v_3|$ maximum 25000 kHz, preferably maximum 20000 kHz, most preferably maximum 10000 kHz.

In an advantageous embodiment, the device of this invention may further comprise a control unit for modulating the energy delivered by the local heating means, e.g. for controlling the radio-frequency energy delivered by the set of radio-frequency focusing coils as a function of the temperature $T_1$ in order to reach and maintain a predefined temperature $T_p$ above the normal mammalian body temperature $T_b$.

According to the embodiments disclosed above, agents, e.g. biologically active agents, suitable for use in the present invention include therapeutic drugs, pharmacologically active agents, nutritional molecules, cosmetic agents, diagnostic agents and contrast agents for imaging. Suitable therapeutic drugs include for example:

antineoplastics and antitumor agents such as, but not limited to, doxorubicin, daunorubicin, carinomycin, N-acetyladriamycin, rubidazone, 5-imidodaunomycin, acetyldaunomycin, epirubicin, vincristine, vinblastine, etoposide, ellipticine, camptothecin, paclitaxel, docetaxol (taxotere), mitotane, cisplatin, and phenesterine, antibiotics, antifungals, anti-inflammatory agents such as, but not limited to, prednisone, methyl-predniso lone, paramethazone, 11-fludrocortisol, triamcinio lone, betamethasone, dexamethasone, ibuprofen, piroxicam, beclomethasone, methotrexate, azaribine, etretinate, anthralin, psoralins or aspirin, immunosuppressive agents such as, but not limited to, cyclosporine, anti-infective agents, antivirals, antihelminthic agents, genes for gene therapy, and antiparasitic compounds.

Other suitable pharmacologic agents include for example:

anaesthetics such as, but not limited to, methoxyflurane, isoflurane, enflurane, halothane and benzocaine, antiulceratives such as, but not limited to, cimetidine, and anti-seizure agents such as, but not limited to, barbituates, and muscle relaxants (such as but not limited to dantrolene and diazepam).

Suitable nutritional molecules include amino acids, sugars, flavoring compounds, proteins, carbohydrates, vitamins and fat among others. Suitable Imaging agents include ultrasound contrast agents, radio-contrast agents (such as radioisotopes or compounds containing radioisotopes), or magnetic contrast agents (such as paramagnetic compounds).

Diagnostic agents include dyes (such as vital blue).

The thermally activatable agents, e.g. biologically active agents, are preferably activated at temperatures above the normal temperature for the mammal of interest, for instance in the case of a human being, above about 37° C. Especially useful are temperatures comprised between 36° and 45° C., preferably between 37° and 41° C., more preferably between 39° and 41° C. The way the agent, e.g. the biologically active agent, is made thermally activatable is not critical for the present invention as long as the agent, e.g. the biologically active agent, is activated in the temperature range cited above. In other words, the agent, e.g. the biologically active agent, must be in an inactive form below the temperature range cited above and in an active form within this temperature range. For example, the agent, e.g. the biologically active agent can be made inactive by binding with one or more other agents, which liberate and therefore activate the agent, e.g. biologically active agent within the temperature range cited above. For example, the agent, e.g. biologically active agent, can be coated with or enclosed within a structure that becomes leaky in this temperature range. Preferably, this structure should be biocompatible. A particular embodiment is the use of a temperature sensitive membrane. Preferably, the membrane should be below microscopic size (e.g. 0.01-1 µm). Suitable membranes include, but are not limited to, liposomes. Liposomes consist of one or more lipid bilayer membrane(s) enclosing an aqueous internal compartment. Liposomes are suitable for the present invention because, although they normally do not leak, they start to release their content when their temperature increases above their gel-to-liquid crystalline phase transition temperature. Also useful for use in the present invention are modified liposomes such as, but not limited to, polymer coated liposomes. The coating of liposome with well-chosen polymers or co-polymers is one of the possible ways to control the temperature at which the liposome will start to leak and the extend of this leakage. A non-limitative example of polymer coated liposome is a liposomal surface coated with a copolymer of N-isopropylacrylamide/octadecylacrylate/acrylic acid such as described in U.S. Pat. No. 5,720,976. Another class of modified liposomes useful for use in the present invention are liposomes modified with surface active agents. This class of liposomes contains in their membrane(s) some agents which modify either the temperature at which the content entrapped in the interior of the liposome is released or the amount and/or the speed at which this content is released. Examples of suitable surface active agents for use in the present invention include, but are not limited to, palmitoyl derivatives, stearoyl derivatives, polyethylene glycol, glyceryl monopalmitate, glyceryl monooleate, ceramides, PEG-ceramides, and therapeutic lipids. Suitable therapeutic lipids include, for example, C-18 ether linked lysophoshatidyl-choline. In a preferred embodiment, the surface agent used in the present invention is a lysolipid such as, but not limited to, monopalmitoyl-phosphatidylcholine.

Any of the membrane classes described above can be further modified by linkage to an agent able to interact specifically with the target specific area where the drug release is desired. For instance, the membrane can be modified with a tumour associated antigen such as the G250 antibody, if the target is renal cell carcinoma.

The location of the one or more agents, e.g. biologically active agents, within the temperature sensitive membrane(s) is not critical for the present invention. Agents, e.g. biologically active agents, can for instance be present in an aqueous solution enclosed by the membrane or within the membrane itself.

The method used for administration of the agent, e.g. biologically active agent, to the mammal can be any usual way to deliver an agent, e.g. a biologically active agent, directly into the bloodstream such as, but not limited to, intravenous transfusion or catheter delivery.

It is an important feature of the present invention that a suitable range of temperature is obtained at a suitable location of the body (e.g. where the agent, e.g. the biologically active agent, is to be released or where a tumour is to be treated). It is equally important that the temperature of other parts of the body which do not have to be treated or which could be damaged by either the drug release or heat, is not raised substantially. It is therefore useful to monitor the temperature of the body or at least of one or more of the relevant parts of the body at various time points of the method, preferably throughout the duration of the whole process. In order to perform this monitoring, the present invention makes use of MRI thermometry measurements, preferably advanced MRI thermometry measurements such as, but not limited to, proton frequency shift based MRI thermometry measurements taking into account fat phase information at the area of interest, and hereinafter referred to as "enhanced proton shift technique". The MRI thermometry measurements are performed by using a radio-frequency monitoring coil, preferably the monitoring coil originally present in all commercial MRI system. This radio-frequency monitoring coil is either a mono-channel or a multi-channel transmitting and receiving component operating at an MR $^1$H larmor frequency $v_1$, i.e. in the range 120-130 MHz for a c.a. 3T basic magnetic field such as, but not limited to, 128 MHz. Means for raising the temperature of the body area where drug release is desired are well known in the art such as, but not limited to, ultrasound, microwave or radio-frequency heating. In the latter case, use may be made of a set of one or more radio-frequency focusing coils, the said set comprising at least two channels. For instance, the set of radio-frequency coils can be made of two or more mono-channel focusing coils or one or more multi-channel focusing coils. The set of radio-frequency focusing coils can also be made of a combination of mono-channel focusing coils and multi-channel focusing coils. In a preferred embodiment, the set of radio-frequency focusing coils is composed of two or more mono-channel focusing coils. In this embodiment, the focusing coils can be ideally placed around and in the vicinity of the selected location of interest. In another preferred embodiment, the set of radio-frequency focusing coils is composed of a single multi-channel radio-frequency focusing coil. The radio-frequency coils useful for heating the selected location of the body which needs to be treated or where the drug is wished to be released are preferably equipped with emission and reception capabilities. A particularly preferred set is therefore a single multi-channel radio-frequency focusing coil equipped with emission and reception capabilities. The set of one or more radio-frequency focusing coils comprises at least two channels operating at preferably another frequency $v_2$ than the monitoring coil for the purpose of delivering focused radio-frequency energy to the selected location and thus for effecting the increase of temperature. Most preferably, the frequency $v_2$ is minimum 50 kHz apart from the frequency $v_1$. This means that $v_1$ and $v_2$ obey one of both following formula:

$$v_2 \leq v_1 - 50 \text{ kHZ, or} \qquad (a)$$

$$v_2 \geq v_1 + 50 \text{ kHz} \qquad (b)$$

The set of one or more radio-frequency coils is composed of multiple elements, each of which is equipped with an antenna capable of both sending and receiving radio-frequency energy at the desired phase and amplitude. In order to localise heat, the incident electromagnetic waves must coincide constructively, i.e. they should possess approaching or identical phase characteristics at that area of interest (and approaching or identical frequency). This can be achieved by performing a "calibration" step before "the focusing step". During calibration, the set of one or more radio-frequency focusing coils is used to transmit radio-frequency excitation pulses to the body at the operating frequency $v_1$, i.e. the larmor frequency for $^1$H, in order to obtain magnetic resonance free induction decay (hereinafter referred as FID) signals back from the body. An example of a sequence that can be used for this purpose includes, but is not limited to, a standard turbo spin echo sequence. The resulting FID signals received by each elements of the set of one or more radio-frequency focusing coils differs in phase and amplitude per element. These signals are also depending on the patient and anatomical region. A control unit determines for each antenna the amplitude and phase of the FID signal received by the antenna and activates the antennas independently of one another for the purpose of emitting radio-frequency radiation at a frequency $v_2$ of phase and amplitude such as to maximise the energy at the selected location by generating a radio-frequency field focused in the volume of the body (i.e. the selected location) where the temperature should be raised and/or the drug should be released. The body penetration depth that can be achieved is highly dependent on the frequency of the emitted radio-frequency waves. For a 3 Tesla MRT system, the radio-frequency is $v_{MR}=v_1=128$ MHz, corresponding to a wavelength range of 10-25 cm which is ideal for focusing the radio-frequency within the mammalian body. $v_2$, which is only 50-25000 kHz apart from $v_1$, is therefore equally good for focussing the radio-frequency within the mammalian body.

In a preferred embodiment of the present invention, the transient local agent, e.g. biologically active agent, concentration level in the area of interest (i.e. the selected location) is monitored. The aim of this monitoring is to establish whether the agent, e.g. the biologically active agent is in a sufficient concentration at the selected location. This permits to avoid heating the body unnecessarily and permits to ensure efficient drug delivery. This monitoring is performed by any suitable method, especially a real time method but preferably by use of a monitoring coil preferably in real time by using an MRI technique. In a specific embodiment of the present invention, the monitoring is done by localised Magnetic Resonance spectroscopy to perform spectroscopic characterisation of the carrier membranes. Alternatively, the drug can be combined with a contrast agent such as, but not limited to, a magnetically responsive material. The imaging methods that can be used to monitor the drug dispersal depend on the contrast agent incorporated in the solution. Examples of magnetically responsive material includes standard gadolinium complexes such as, but not limited to, gadolinium (III) diethylenetriamine-pentaacetic acid (Gd-DTPA) or Gd impregnated microspheres. In this case, the monitoring can for instance be performed by using ultra fast real-time imaging methods such as, but not limited to, T1 weighted fast field echo sequence. Alternatively, the drug can be combined with a non proton based hyper-polarised substance such as, but not limited to, $^{13}$C, $^{15}$N, $^{31}$Na, or $^{19}$F-containing substances. In the case of $^{13}$C, the monitoring can for instance be performed by using true fast imaging with steady-state precession pulse sequence. Both the monitoring coil and the focusing coil(s) are preferably operating together. This is enabled by offsetting $v_2$ by at least 50 kHz in comparison to $v_1$ in order to avoid undesired interference.

Figure 1:
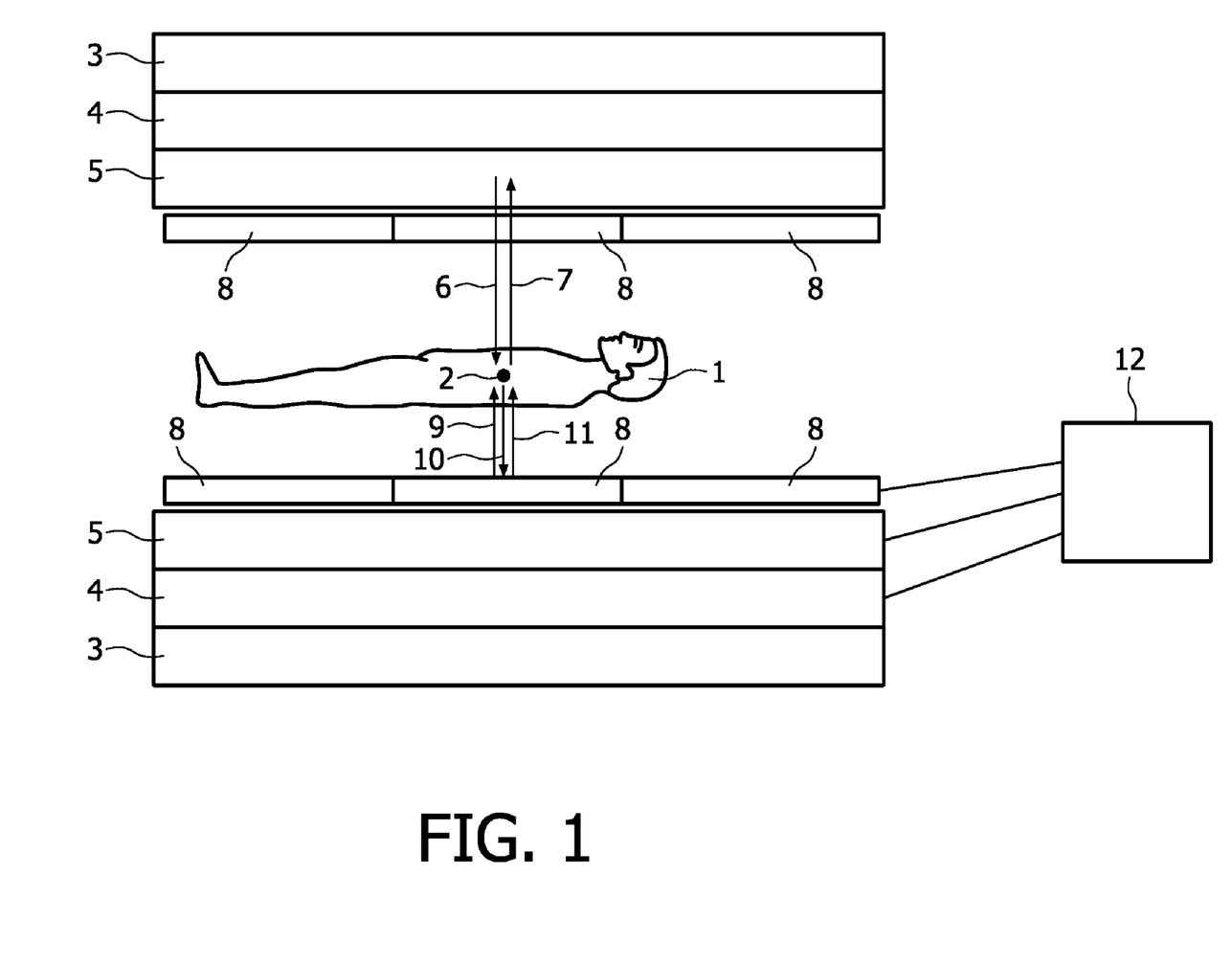
FIG. 1 is a schematic illustration of a side view of an example of device according to one embodiment of the present invention.

FIG. 1 schematically shows the cross-section of a device according to an embodiment of the present invention. In the middle of the scheme, a human body (1) is represented with a selected location (2) where, optionally, an agent, e.g. a biologically active agent enclosed in a temperature sensitive structure is intended for release. At the bottom and at the top of the drawing, cross-sections of four different elements are represented. The element (3) is a magnet of a classical MRI system. The second element (4) next to the magnet (3) is a gradient coil of a classical RMI system. The third element (5)

next to the gradient coil (4) is the radio-frequency monitoring coil of a classical MRI system. This radio-frequency monitoring coil is capable to emit and receive radio-frequency waves such as (6) and (7). The fourth element (8), which is here represented closest to the body (1), is a multi-channels radio-frequency focusing coil (8). Six channels (three represented above the body and three represented below the body) of the radio-frequency focusing coil (8) are represented, each of these channels having the capacity to emit and to receive radio-frequency waves such as (9), (10) and (11). A controller (12) is connected to the gradient coil (4), the radio-frequency monitoring coil (5) and the multi-channel radio-frequency emitting coil (8). The arrow (6) represents radio-frequency waves emitted from the radio-frequency monitoring coil (5) to the selected location (2) for the purpose of gaining information concerning either the temperature of the selected location (2) or the concentration of the agent, e.g. the biologically active agent, at this selected location (2). The arrow (7) represents the modified signal coming back from the selected location (2). Once this signal (7) has been received by the radio-frequency monitoring coil (5), it is sent to the controller (12) where it will be analysed and will deliver information concerning either the temperature of the selected location (2) or the concentration of the agent, e.g. the biologically active agent at this selected location (2) depending on the Resonance Magnetic method used for the generation and the analysis of radio-frequency waves (6) and (7). For the sake of clarity, the next processes will be illustrated for only one of the six channels of the multi-channel radio-frequency focusing coil (8). It must nevertheless be understood that this same process operates simultaneously with the six channels of the multi-channel radio-frequency focussing coil (8). Arrow (9) represents radio-frequency waves of phase $\phi_1$ and amplitude $\alpha_1$ emitted from one of the channels of the multi-channel radio-frequency focussing coil (8). These radio-frequency waves (9) are emitted for the purpose of determining the optimal phase and amplitude necessary to deliver a maximum of energy at the selected location (2). The radio-frequency waves (10) are generated at the selected location (2) and are received by the same single channel of the multi-channel radio-frequency focussing coil (8). Once this signal has been received, it is sent to the controller (12) where it is analysed and delivers information concerning the optimal phase $\phi_2$ and amplitude $\alpha_2$ necessary to provide optimal energy at the selected location (2). Finally, the radio-frequency waves (11) are sent from the same single channel of the multi-channel radio-frequency focussing coil (8) to the selected location (2) with the optimal phase $\phi_2$ and amplitude $\alpha_2$.

Figure 2:
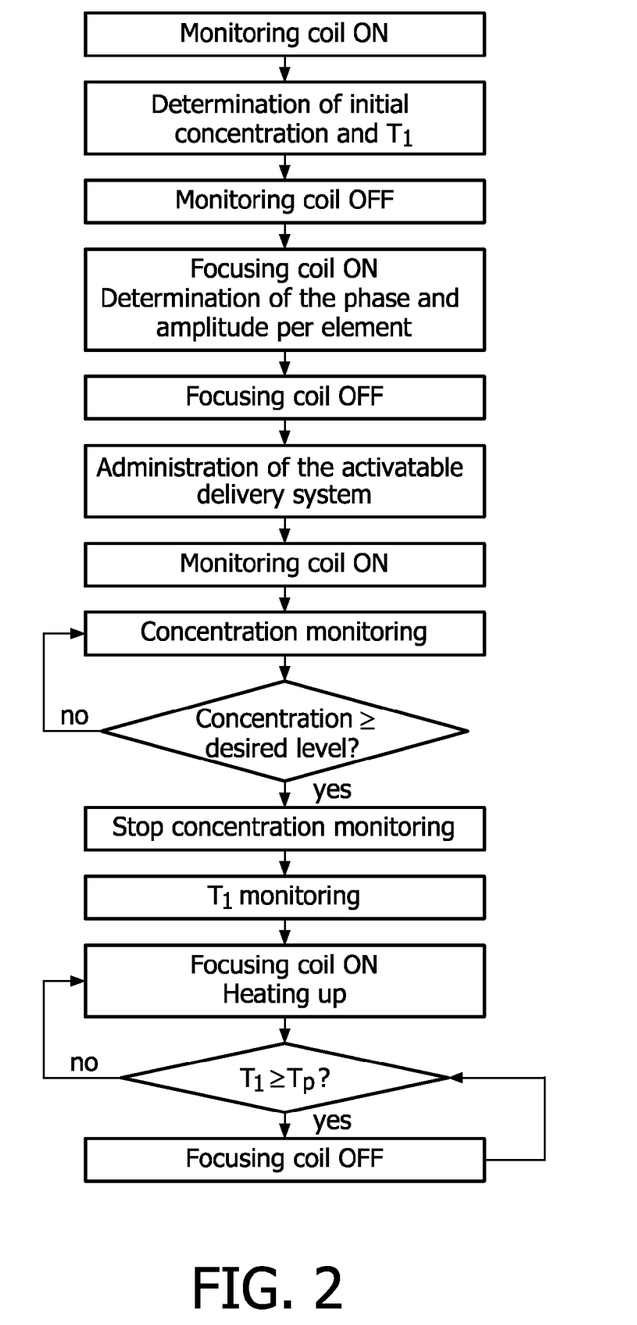
FIG. 2 is a flow-chart diagram describing a method according to an embodiment of the present invention.

FIG. 2 shows a flow-chart diagram describing a method according to an embodiment of the present invention. First, the monitoring coil is turned on in order to determine the initial concentration in agent, e.g. biologically active agent, (e.g. zero) and the temperature at the selected location $T_1$. Both determinations are performed one after the other without any particular order. Then, the monitoring coil is turned off, the focussing coil is turned on and performs the determination of the optimal phase and amplitude per element necessary to deliver a maximum of energy at the selected location (as described in FIG. 1 and above). The focusing coil is then turned off and the activatable delivery system (e.g. an agent, e.g. a biologically active agent, enclosed in a thermosensible structure) is administered to the mammalian body. Both steps can be performed either separately in any order or together. In the next step, the monitoring coil is turned on for the purpose of monitoring the activatable delivery system concentration. As long as this concentration does not equal or exceed the desired/adequate concentration, the monitoring of the concentration is continued. Once the desired/adequate concentration is achieved or exceeded, the concentration monitoring is stopped and the monitoring coil starts to monitor the local temperature $T_1$. The focusing coil is then turned on for the purpose of heating up the selected location. This heating up process is performed simultaneously with the monitoring of the temperature $T_1$ and is continued as long as $T_1$ does not equal or exceed the predetermined temperature $T_p$. Once this temperature $T_p$ exceeded or equalled, the focusing coil is turned off while the temperature is still monitored. The focusing coil remains turned off as long as $T_1$ is equal or exceed $T_p$ and is turned on again as soon as it is no longer the case. The local temperature is therefore maintained at $T_p$.

Figure 3:
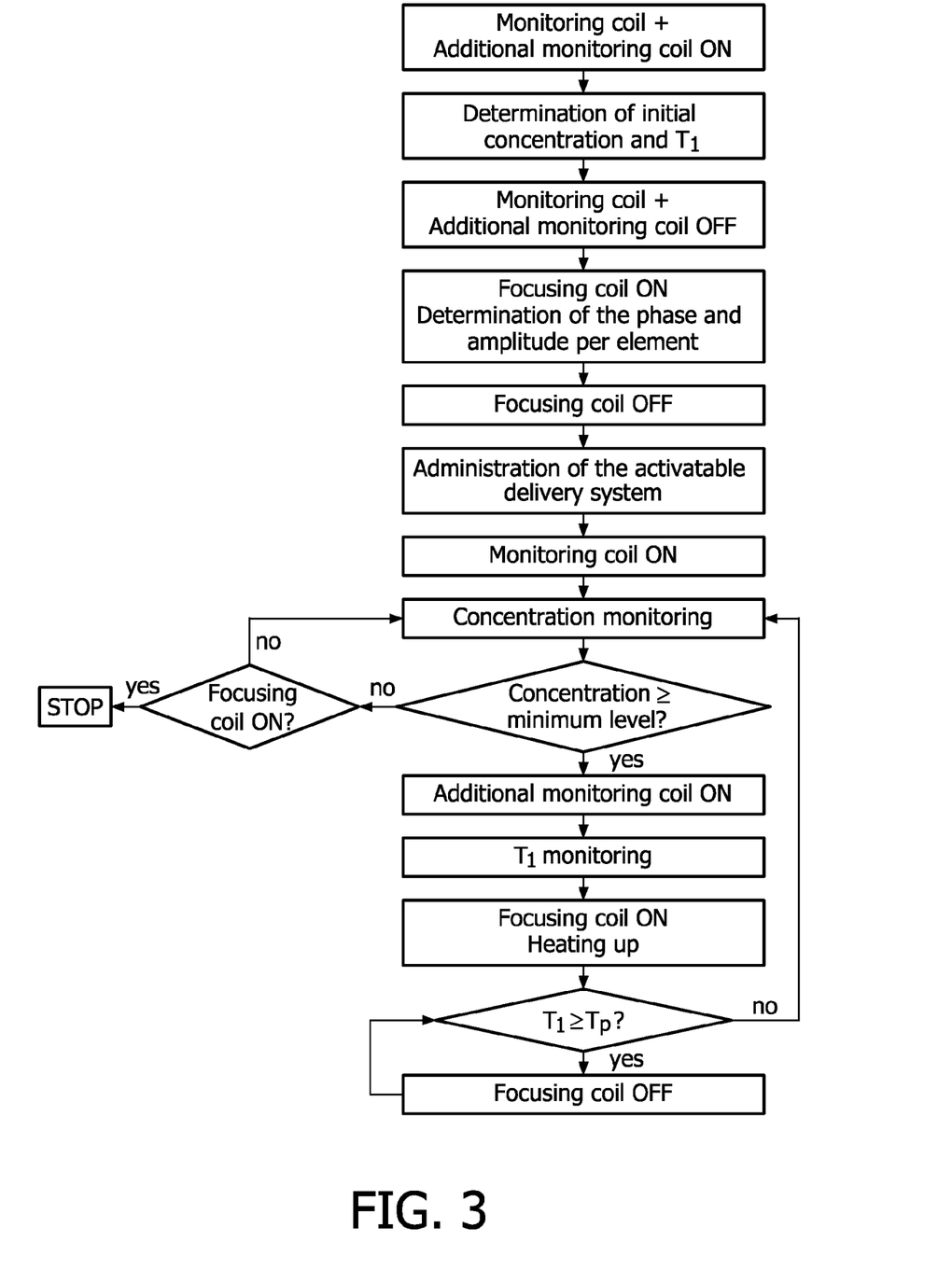
FIG. 3 is a flow-chart diagram describing a method according to an embodiment of the present invention.

FIG. 3 shows a flow-chart diagram describing a method according to another embodiment of the present invention. First, the monitoring coil (e.g. the monitoring coil originally present in a commercial MRI system) and an additional monitoring coil are turned on fur the purpose of determining the initial concentration of an agent, e.g. a biologically active agent, (e.g. zero) and the temperature at the selected location $T_1$. Here, both determinations may (but do not have to) be performed simultaneously. Once both monitoring coils are turned off, the focusing coil is turned on for determining the optimal phase and amplitude per element necessary to deliver a maximum of energy at the selected location. Then, the focusing coil is turned off. Next, the activatable delivery system is administered to the mammalian body and one of both monitoring coils is turned on for monitoring the concentration of the activatable delivery system in the body. As long as this concentration is strictly below the desired level, the monitoring of the concentration is continued. Once the desired level is achieved, the monitoring coil which is not turned on yet (e.g. the additional monitoring coil) is turned on for monitoring the local temperature at the selected location. Next, the focusing coil is turned on, without turning off any of both monitoring coils, in order to heat up the selected location. As long as the local temperature $T_1$ does not exceed or equal the predefined temperature $T_p$ and as long as the concentration remains equal or superior to the desired level, the heating up process is maintained. As soon as the local temperature exceeds the predefined temperature, the focusing coil is switched off and remains in this state as long as the local temperature $T_1$ exceeds or equal the predefined temperature $T_p$. When the local temperature $T_1$ comes back below the predefined temperature $T_p$. The focusing coil is switched on again and the heating process re-starts. If at any time, the concentration drops below the desired concentration, the whole process stops definitively.

The following examples are provided for illustration of the invention without any limiting intention.

Example 1

A device such as shown in FIG. 1 was used. The magnetic field was 3T. First, a reference step is effected during which the radio-frequency monitoring coil initiates appropriate pulse sequences in order to acquire data and establish:
a) temperature difference maps, e.g. based on a proton frequency shift method taking into account fat phase information at a selected location, and
b) the initial concentration of a membrane enclosing an active agent at this selected location by using localised Magnetic Resonance spectroscopy.

Secondly, a calibration step is effected during which the selected location is selected and each element of the radio-frequency focusing coil is used to transmit radio-frequency excitation pulses at 128.0 MHz, in order to obtain Magnetic Resonance FID signals. Each resulting FID signal is received by each of the elements of the focusing coil, and differs in terms of phase and amplitude per element.

Thirdly, an agent, e.g. a biologically active agent, administration step is started during which, a biologically active agent solution, encapsulated within lysolipid-containing heat-sensitive liposomes, is transfused to the patient intravenously.

Fourthly, an agent, e.g. a biologically active agent, monitoring step is started during which the concentration of the agent, e.g. biologically active agent, at the area of interest is monitored by a radio-frequency monitoring operating at 128.0 MHz for the purpose of determining when the agent, e.g. biologically active agent, is in a sufficient concentration at the area of interest.

Fifth, a focusing step is started during which the radio-frequency focusing coil operates as a transmission unit and the radio-frequency energy at 128.1 MHz is emitted from its elements based on the individual phase and amplitude parameters obtained during the calibration step. The energy is thus focused and deposited only in the selected location of interest and therefore leads to the desired temperature increase to effect the release of the agent, e.g. biologically active agent, without harming other body locations.

Simultaneously with the fifth step, a control step is started during which the radio-frequency monitoring coil is used as in the reference step to evaluate the temperature gradients developed during the focusing step. This step essentially controls when the focusing step must be stopped or re-started in order to keepl the desired temperature.

Example 2

A device such as shown in FIG. 1 was used. The magnetic field was 2T. First, a reference step is started during which the radio-frequency monitoring coil initiates appropriate pulse sequences in order to acquire data and establish:
a) temperature difference maps, e.g. based on a proton frequency shift method taking into account fat phase information at a selected location, and
b) the initial concentration of a gadolinium impregnated trisacryl gelatin microspheres agent, at a selected location of the body.

Secondly, a calibration step is started during which the target selected location is selected and the radio-frequency focusing coil is used to transmit radio-frequency excitation pulses at 128 MHz, in order to obtain Magnetic resonance FID signals via a standard turbo spin echo sequence. The resulting FID signal is received by each of the elements of the radio-frequency focusing coil, and differ in terms of its phase and amplitude per element.

Thirdly, an agent, e.g. biologically active agent, administration step is performed during which a drug solution together with gadolinium impregnated trisacryl gelatin microspheres agents, encapsulated in carrier lysolipid-containing temperature-sensitive liposomes, are transfused to the patient via a catheter delivery method. At the same time, a T1 weighted fast field echo sequence imaging method is used to monitor the concentration of the microspheres contained within the drug solution by using the radio-frequency monitoring coil. Once the concentration reaches the desired level, the fourth phase is initiated.

Fourthly, a focusing step is started during which the focusing coil operates as a transmission element and the radio-frequency energy is emitted from its elements based on the individual phase and amplitude parameters obtained during the calibration phase. The energy is thus focused and deposited only in the selected location of the mammalian body and therefore leads to the desired temperature increase to effect the drug release.

Simultaneously with the fourth step, a control step is started during which the monitoring coil is used as in the reference step to evaluate the temperature gradients developed during the focusing step. This step essentially controls When the focusing step must be stopped or re-started in order to keep the desired temperature.

Example 3

A device such as shown in FIG. 1 was used, wherein the monitoring coil is capable of imaging both $^1$H and $^{13}$C. First a reference step is started during which the radio-frequency monitoring coil initiates appropriate pulse sequences in order to acquire data and establish:
temperature difference maps, e.g. based on a proton frequency shift method taking into account fat phase information at a selected body location, and
the initial concentration of the $^{13}$C impregnated agent, at the selected location.

Secondly, the calibration step is started during which the selected location is chosen and the radio-frequency focusing coil is used to transmit radio-frequency excitation pulses at 128 MHz, in order to obtain MR FID signals via a standard turbo spin echo sequence. The resulting FID signal is received by each of the elements of the radio-frequency focusing coil, and differ in terms of its phase and amplitude per element.

Thirdly, an agent, e.g. biologically active agent, administration step is started during which, an agent, e.g. a biologically active agent, solution together with a $^{13}$C rich agent, encapsulated in carrier lysolipid-containing temperature-sensitive liposomes, are transfused to the patient via a catheter delivery method. At the same time, a true fast imaging with steady-state precession pulse is used to monitor the concentration of the drug agent by using the radio-frequency monitoring coil. Once the concentration reaches the desired level, the fourth phase is initiated.

Fourthly, focusing step is started during which the radio-frequency focusing coil operates as a transmission unit coil and the radio-frequency energy is emitted from its elements based on the individual phase and amplitude parameters obtained during the calibration phase. The energy is thus focused and deposited only in the selected location and therefore leads to the desired temperature increase to effect the drug release.

Simultaneously with step four, a control step is started during which the radio-frequency monitoring coil is used to as in the reference step to evaluate the temperature gradients developed during the focusing step. This step essentially controls the duration of the focusing step and therefore both steps are performed simultaneously until the desired temperature is reached.

The invention claimed is:
1. A radio frequency unit, comprising:
(i) a magnetic resonance imaging device comprising a radio-frequency monitoring coil, the radio-frequency monitoring coil measuring a temperature $T_1$ at a selected location of a mammalian body and operating at a frequency $v_1$, wherein the frequency $v_1$ is a Larmor frequency of a $^1$H nucleus and is between 120 and 130 MHz,
(ii) one or more radio-frequency focusing coils delivering focused energy to said selected location of said mammalian body and raising the temperature $T_1$ thereof, said one or more radio-frequency focusing coils comprising at least two channels and operating at a frequency $v_2$ at least 50 kHz apart and at most 25000 kHz apart from the frequency $v_1$ of said radio-frequency monitoring coil, and (iii) a controller modulating said focused energy delivered by said one or more radio-frequency focusing coils as a function of said temperature $T_1$ to reach and maintain a predefined temperature $T_p$ above a normal mammalian body temperature $T_b$.

2. The radio frequency unit according to claim 1, wherein said one or more radio-frequency focusing coils: 1) provide energy at said selected location of said mammalian body and operate at said frequency $v_1$; and 2) receive signals containing location-dependent phase information and location-dependent amplitude information, during a calibration stage of said one or more radio-frequency focusing coils.

3. A radio frequency unit, comprising:
(i) a magnetic resonance imaging device comprising a radio-frequency monitoring coil, the radio-frequency monitoring coil measuring a temperature $T_1$ at a selected location of a mammalian body and operating at a frequency $v_1$, wherein the frequency $v_1$ is a Lamor frequency of a $^1H$ nucleus and is between 120 and 130 MHz,
(ii) one or more radio-frequency focusing coils delivering focused energy to said selected location of said mammalian body and raising the temperature $T_1$ thereof, said one or more radio-frequency focusing coils comprising at least two channels and operating at a frequency $v_2$ at least 50 kHz apart and at most 25000 kHz apart from the frequency $v_1$ of said radio-frequency monitoring coil,
(iii) a controller modulating said focused energy delivered by said one or more radio-frequency focusing coils as a function of said temperature $T_1$ to reach and maintain a predefined temperature $T_2$ above a normal mammalian body temperature $T_b$, and
(iv) an additional monitoring coil operating at a frequency $v_3$ monitoring a transient concentration of one or more agents at said selected location of said mammalian body, wherein the frequency $v_3$ is a Larmor frequency of a nucleus other than the $^1H$ nucleus and is at least 50 kHz apart and at most 25000 kHz apart from the frequency $v_2$.

4. The radio frequency unit according to claim 2, wherein the controller determines from said location-dependent phase information and said location dependent amplitude information, for each channel of said one or more radio-frequency focusing coils, a phase and/or an amplitude required for emitting radio-frequency energy from said each channel to produce maximal radio-frequency energy from said each channel at said selected location of said mammalian body.

5. A system for thermodynamic therapy comprising:
(i) a set of one or more radio-frequency focusing coils which focus energy at a frequency $v_2$ at a selected location of a mammalian body to locally raise a temperature $T_1$ of said mammalian body at the selected location until a predefined temperature $T_p$ is obtained, and
(ii) a controller which monitors the temperature $T_1$ of the selected location of the mammalian body by a Magnetic Resonance Imaging technique operating at a frequency $v_1$ simultaneously with said raising of said temperature $T_1$ of said selected location of the mammalian body, wherein an absolute difference of the frequency $v_2$ and the frequency $v_1$ is between 50 to 25000 kHz, and wherein the frequency $v_1$ is a $^1H$ Lamor frequency between 120 and 130 MHz.

6. The system according to claim 5 further including:
a thermally activatable delivery system, the thermally activatable delivery system releasing one or more agents at the selected location of the mammalian body in response to the temperature $T_1$ of said selected location of said mammalian body being raised to the predefined temperature $T_p$ above a normal mammalian body temperature $T_b$, wherein the Magnetic Resonance Imaging technique operates to monitor a transient concentration of said one or more agents at said selected location of said mammalian body.

7. The radio frequency unit according to claim 1, wherein said magnetic resonance imaging device is configured to utilize an enhanced proton shift technique, the enhanced proton shift technique taking in to account fat phase information for thermometry measurements.

8. An arrangement for thermodynamic therapy comprising:
the radio frequency unit according to claim 1, and
a thermally activatable delivery system which releases one or more agents administered to said mammalian body, said one or more agents administered before said temperature of said selected location of said mammalian body is raised, and said one or more agents being released at the selected location of said mammalian body in response to the temperature $T_1$ of said selected location of said mammalian body being raised to the predefined temperature $T_p$ above the normal mammalian body temperature $T_b$,
wherein said radio frequency unit monitors a transient concentration of said one or more agents at said selected location of said mammalian body by a Magnetic Resonance Imaging technique involving said radio-frequency monitoring coil.

9. The arrangement according to claim 8, wherein at least one of the agents are enclosed within a temperature sensitive structure which releases said at least one of the agents in response to the temperature $T_1$ being raised to the predefined temperature $T_p$ above the normal mammalian body temperature $T_b$.

10. The arrangement according to claim 8, wherein $36°C. \leq T_p \leq 45°C$.

11. The arrangement according to claim 9, wherein said temperature sensitive structure is a temperature sensitive membrane.

12. The arrangement according to claim 11, wherein said temperature sensitive membrane comprises a liposome.

13. The arrangement according to claim 12, wherein said liposome comprises a lysolipid-containing liposome.

14. The arrangement according to claim 8, wherein said one or more agents is selected from a group consisting of antineoplastic agents, antitumor agents, antibiotics agents antifungals agents, anti-inflammatory agents, immunosuppressive agents, anti-infective agents, antivirals agents, anthelminthic agents, gene for gene therapy and antiparasitic agents.

15. The arrangement according to claim 8, wherein said radio frequency unit monitors said transient concentration of said one or more agents at said selected location of said mammalian body by Magnetic Resonance spectroscopy.

16. The arrangement according to claim 8, wherein said thermally activatable delivery system includes one or more agent concentration markers.

17. The arrangement according to claim 16 wherein said one or more agent concentration markers are selected from a group consisting of gadolinium solutions, gadolinium-impregnated microspheres, $^{13}C$, $^{15}N$, $^{31}P$, $^{23}Na$ and $^{19}F$ containing species.

18. The arrangement according to claim 16, wherein the radio frequency unit controls the transient concentration by monitoring said one or more agent concentration markers by means of the Magnetic Resonance Imaging technique.

19. The arrangement according to claim 8, wherein said one or more radio-frequency focusing coils includes at least one of:
  two or more mono-channel radio-frequency coils; and
  one or more multi-channel radio-frequency coils.

20. The radio frequency unit according to claim 1, wherein said one or more radio-frequency focusing coils are different than said radio-frequency monitoring coil.

* * * * *